United States Patent
Barfoot et al.

(10) Patent No.: US 10,309,213 B2
(45) Date of Patent: Jun. 4, 2019

(54) DISTRIBUTED OPTICAL SENSING USING COMPRESSIVE SAMPLING

(71) Applicant: Halliburton Energy Services, Inc., Houston, TX (US)

(72) Inventors: David Andrew Barfoot, Houston, TX (US); Satyan Gopal Bhongale, Cypress, TX (US); Christopher Lee Stokely, Houston, TX (US); Andreas Ellmauthaler, Rio de Janeirio (BR)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/526,657

(22) PCT Filed: Dec. 28, 2015

(86) PCT No.: PCT/US2015/067598
§ 371 (c)(1),
(2) Date: May 12, 2017

(87) PCT Pub. No.: WO2017/116383
PCT Pub. Date: Jul. 6, 2017

(65) Prior Publication Data
US 2018/0058197 A1    Mar. 1, 2018

(51) Int. Cl.
| E21B 47/10 | (2012.01) |
| G01V 8/02 | (2006.01) |
| G01V 8/10 | (2006.01) |
| E21B 47/12 | (2012.01) |
| G01D 5/353 | (2006.01) |
| G01N 21/03 | (2006.01) |

(Continued)

(52) U.S. Cl.
CPC .......... E21B 47/102 (2013.01); E21B 47/123 (2013.01); G01D 5/35358 (2013.01); G01N 21/03 (2013.01); G01V 8/02 (2013.01); G01V 8/10 (2013.01); G01V 8/24 (2013.01); G01N 2021/0364 (2013.01); G01V 8/22 (2013.01)

(58) Field of Classification Search
CPC . E21B 47/102; E21B 47/123; G01D 5/35358; G01N 21/03; G01V 8/24
USPC .......................................... 250/227.14, 221
See application file for complete search history.

(56) References Cited

U.S. PATENT DOCUMENTS 5,166,747 A * 11/1992 Schroeder ............. E21B 47/102
                                                           250/256
6,078,414 A    6/2000 Iwano
(Continued)

OTHER PUBLICATIONS

International Search Report and the Written Opinion of the International Search Authority, or the Declaration, dated Sep. 23, 2016, PCT/US2015/067598, 14 pages, ISA/KR.

(Continued)

*Primary Examiner* — Que Tan Le
(74) *Attorney, Agent, or Firm* — Haynes and Boone, LLP (57) ABSTRACT

Distributed optical sensing systems utilize compressive sensing techniques to determine parameters sensed by a waveguide. The system generates light that is sent along a sensing waveguide, thereby producing backscattered light. A compressive sampling filter forms part of the system, and is used to selectively block portions of the generated light or the backscattered light. The backscattered light is received by a receiver and used to determine one or more parameters.

26 Claims, 5 Drawing Sheets

(51) Int. Cl.
*G01V 8/24* (2006.01)
*G01V 8/22* (2006.01)

(56) References Cited

U.S. PATENT DOCUMENTS

| | | |
|---|---|---|
| 7,274,441 B2 | 9/2007 | Payton |
| 2009/0097015 A1 | 4/2009 | Davies et al. |
| 2010/0207019 A1 | 8/2010 | Hartog et al. |
| 2011/0199607 A1 | 8/2011 | Kanellopoulos et al. |
| 2012/0067118 A1 | 3/2012 | Hartog et al. |
| 2012/0105826 A1 | 5/2012 | Kalar et al. |
| 2012/0162639 A1 | 6/2012 | Farhadiroushan et al. |

OTHER PUBLICATIONS

Candès, Emmanuel J., "Compressive Sampling," *In Proceedings of the International Congress of Mathematicians*, vol. 3, pp. 1433-1452, Aug. 22, 2006.

Candès, et al., "An Introduction to Compressive Sampling," *IEEE Signal Processing Magazine*, vol. 25, No. 2, pp. 21-30, Mar. 25, 2008.

Johnson, Dexter, "Nanoscale Metamaterial Optical Switches Operate at Terahertz Speeds," *IEEE Spectrum*, Mar. 14, 2014.

Posey, et al., "Strain Sensing Based on Coherent Rayleigh Scattering in an Optical Fibre," *Electronics Letters*, vol. 36, No. 20, pp. 1688-1689, Sep. 28, 2000.

Smolen, et al., "A DTS Primer for Oil & Gas Production," Shell International Exploration and Production: The Hague, The Netherlands, May 2003.

Ukil, et al., "Distributed Temperature Sensing: Review of Technology and Applications," *IEEE Sensors Journal*, No. 5, vol. 12, May 2012.

Wakin, et al., "An Architecture for Compressive Imaging," In *Image Processing, 2006 IEEE International Conference on*, pp. 1273-1276, Oct. 8, 2006.

\* cited by examiner

FIG. 5 ic fiber optic sensing, an unmodified fiber optic waveguide is used as a sensor. There are many ways to interrogate a distributed fiber optic sensor, but all of these methods require sending optical energy into the fiber to produce a backscattering of the light which is used to measure a physical property in proximity to the fiber, such as, temperature, vibration, static or dynamic strain, chemical concentration, or pressure. Examples of commercially established methods include distributed temperature sensing ("DTS"), distributed acoustic sensing ("DAS"), and distributed strain sensing ("DSS").

DISTRIBUTED OPTICAL SENSING USING COMPRESSIVE SAMPLING

PRIORITY

The present application is a U.S. National Stage patent application of International Patent Application No. PCT/US2015/067598, filed on Dec. 28, 2015, the benefit of which is claimed and the disclosure of which is incorporated herein by reference in its entirety.

FIELD OF THE DISCLOSURE

The present disclosure relates generally to optical sensing and, more specifically, to an optical sensing using compressive interrogation methods.

BACKGROUND

In distributed fiber optic sensing, an unmodified fiber optic waveguide is used as a sensor. There are many ways to interrogate a distributed fiber optic sensor, but all of these methods require sending optical energy into the fiber to produce a backscattering of the light which is used to measure a physical property in proximity to the fiber, such as, temperature, vibration, static or dynamic strain, chemical concentration, or pressure. Examples of commercially established methods include distributed temperature sensing ("DTS"), distributed acoustic sensing ("DAS"), and distributed strain sensing ("DSS").

In such systems, it is desirable to spatially divide the fiber optic cable, which may be many kilometers long, into discrete sensing regions so that the cable is transformed into a dense array of sensors. These sensors are not placed in or attached to the fiber, but instead are created by the way the fiber is interrogated. Ideally, the dense array of sensors will have spacing between the sensors down to the level of a few meters or less if possible, so as to achieve a very fine spatial resolution. This is of particular importance when sensing along the length of a wellbore, where features of interest may be very localized and in close proximity to areas with different properties. For example, wellbore features like perforation clusters, packers, and production zones may need to be spatially separated in any effective measurement.

In distributed sensing, when a light interrogation signal is sent into the fiber, as the light is travelling down the fiber, a continuous backscatter signal is generated. The backscatter signal of interest may consist of one or a combination of Rayleigh, Brillouin, or Raman backscatter. In order to provide an array of sensors spaced closely along the fiber, a method of multiplexing, or dividing up the backscatter response from these sensing regions must be utilized. Well known methods for optical spatial multiplexing include time domain multiplexing, frequency domain multiplexing, and code-division multiplexing.

However, the data storage and processing requirements of conventional systems are disadvantageous. In order to achieve a desired spatial resolution, the optical receiver must detect and sample the backscattered signal at a high speed. As a result, high speed and bandwidth system components are necessary. However, as the bandwidth increases, the performance of the receiver will be degraded by a proportional amount, thereby adversely affecting the integrity of the sensed parameters.

DESCRIPTION OF ILLUSTRATIVE EMBODIMENTS

Illustrative embodiments and related methods of the present disclosure are described below as they might be employed in a distributed optical sensing system using compressive sensing. In the interest of clarity, not all features of an actual implementation or methodology are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. Further aspects and advantages of the various embodiments and related methodologies of the disclosure will become apparent from consideration of the following description and drawings.

As described herein, illustrative embodiments of the present disclosure are directed distributed optical sensing systems which utilize compressive sensing techniques. In a generalized embodiment, the sensing system includes a light source to generate light that is sent along a sensing waveguide, thereby producing backscattered light. A compressive sampling filter forms part of the system, and is used in a variety of ways to selectively block portions of the light generated by the light source or the backscattered light. The backscattered light is then received by one or more optical receivers and used by processing circuitry to determine a parameter being sensed by the waveguide. Accordingly, as described herein, a system is provided that utilizes compressive sensing to enhance the performance of distributed fiber optic sensors, while simultaneously reducing data storage and bandwidth requirements by a significant amount. Alternatively, embodiments of the present disclosure may be considered as providing data compression embedded in the sensing device itself. Furthermore, such advantages also translate into higher resolution, when compared to conventional systems, without increasing the sampling rate.

As previously mentioned, there are various methods for optical spatial multiplexing. Although applicable to others, the illustrative embodiments and methods described herein will focus on time domain multiplexing. In an optical time-domain reflectometer, a short duration (i.e., 10 ns) optical pulse is sent into a fiber optic sensing cable or other waveguide. As the light pulse travels down the length of the fiber, it generates a continuously backscatter signal from a continuum of points along the fiber which can be separated in time as it arrives back at the optical interrogation system.

To achieve a desired spatial resolution, an optical receiver will detect and sample the backscatter signal at a high speed. In typical fiber optic systems, the light will travel at approximately 5 ns per meter in the fiber. Therefore, the two-way travel time of the interrogation light to travel from the interrogation system, arrive at a particular location, and subsequently for the backscatter from that location to arrive back at the optical interrogation unit is 10 ns per meter (5 ns/meter in each direction). If the optical signal is sampled by the receiver every 10 ns, or at 100 MHz, the backscatter from each one meter section of fiber will be sampled separately, leading to a dense array of sensors with the center of each sensing region spaced one meter apart. For example, with a 10 km long fiber optic cable, a 100 MHz sample rate will provide 10,000 discrete sensors.

From this description, if it is desirable to increase the spatial resolution of the sensor array by reducing the spacing between the sensing regions, the optical backscatter signal must be sampled at a faster rate. For example, to achieve a 10 cm spacing between the sensing regions, the backscatter must be sampled at 1 GHz. For smaller spacing between sensing regions, a higher rate would be needed.

In order to achieve a high spatial resolution in general, both the optical receiver and analog-to-digital converter ("ADC") must support a bandwidth compatible with the sampling rate required for the desired spatial resolution. For example, in a typical system with one meter spatial resolution, the optical receiver will be designed to have at least a 100 MHz bandwidth. The ADC will be required to sample at least twice this rate, or 200 Mega samples per second ("MSPS"), based on the Nyquist criteria requiring sampling at twice the frequency of the highest frequency component of the signal to prevent aliasing which would translate into an undesirable noise added to the signal being measured.

While in theory it is possible to achieve very high spatial resolution with the time domain multiplexing method, many compromises must be made when increasing the bandwidth of optical receivers and electronic components following the receiver, including amplifiers and ADCs. A typical optical receiver will have a gain (typically a trans-impedance gain), and saturation power level (maximum optical power above which the receiver will not function correctly), and background noise or self-noise (often given in terms of Noise Equivalent Power or "NEP"). As the bandwidth of the receiver is increased, many or all of these other parameters will be degraded due to the required changes to the device to achieve higher bandwidth.

Typically, the product of the gain and bandwidth is a constant for any particular type of optical receiver. This is referred to as the "gain-bandwidth product." Therefore, as the bandwidth is increased, the gain must be reduced by a proportional amount. Because the backscatter signals are very weak compared to the interrogation signal, high gain for the optical receiver is very important in most applications. In addition, low self-noise is important. The NEP may also be degraded when the bandwidth of the receiver is increased. Similar compromises are made with ADCs. For example, to precisely convert an electrical voltage into a digital number, the voltage must be converted into a series of bits. The more bits that are available, the more precisely the voltage can be digitized for later computations. If the number of bits available is too low for the particular measurement, quantization noise becomes a dominant source of noise. Typically, the number of bits available for a commercial ADC is inversely proportional to the maximum sample rate. For example, today many ADCs are available at 100 MSPS with 16-bits of resolution. At speeds over 1 GSPS, more commonly 8-bit or 12-bit ADCs can be found, but not the 16-bit ADCs that are desirable for many applications of fiber optic sensing.

In view of the foregoing, the illustrative embodiments and methods described herein use lower speed and bandwidth components that provide increased performance in terms of gain, dynamic range, and resolution, while simultaneously maintaining a desirable spatial resolution for a particular application. To achieve this, the present disclosure applies compressive signal sampling techniques, also referred to as compressive sensing or compressed sensing. One example of compressive sampling in use is with a single pixel camera, such as described in K. Kelly, et. al., "*An Architecture for Compressive Imaging,*" 2006 IEEE international Conference on Image Processing, Oct. 8-11, 2006, pg. 1273-1276. The main idea of compressive sampling is, instead of measuring all components of a signal separately (by high-speed sampling or by using a sensor array as in a camera), many, but not all of the components of a signal are combined into a single measurement. These composite measurements are performed many times, where in each case, the components (pixels, etc.) that are combined together into the measurement are in most cases randomly chosen using a pseudo-random spatial light filtering method.

In the single pixel camera sampling method, an image is acquired using a single pixel camera. Each measurement includes the combined signal components of what would normally be sensed at many different pixel locations. An array of mirrors is modulated for each measurement so that a pseudo-random combination of pixel locations is combined together at a single optical sensor. By taking many measurements, but far fewer than the total number of image pixels in the final image, it is possible through compressive sampling signal recovery methods, such as, for example, those described in E. Candes, M. Wakin; "*An Introduction to Compressive Sampling,*" IEEE Signal Processing Magazine, March 2008 pg. 21-30 and K. Kelly, et. al., "*An Architecture for Compressive Imaging,*" 2006 IEEE international Conference on Image Processing, Oct. 8-11, 2006, pg. 1273-1276, to reconstruct the full image signal from these single pixel samples.

Turning to illustrative embodiments of the present disclosure, in distributed fiber optic sensing, the spatial samples of an image can be looked at as equivalent if the spatial domain is transformed into the time domain. In other words, the spatial separation of fiber sensors translates to time at a single photodetector/receiver of an interrogation system. Replacing the conventional high-bandwidth receiver system with a low-bandwidth receiver system of the present disclosure would cause the signals from many adjacent fiber sensors to be combined together into a single measurement. This is similar to what happens with the single pixel camera when an array of signals assigned to different pixels is combined into a single pixel detector. In the case of the single-pixel camera, micro-mirrors are used to allow only some of the pixels to be received at the detector instead of all of them. As will be described in detail below, the illustrative embodiments herein utilize a compressive sampling filter to perform this same function, thereby selectively blocking certain portions of backscattered light.

Figure 1:
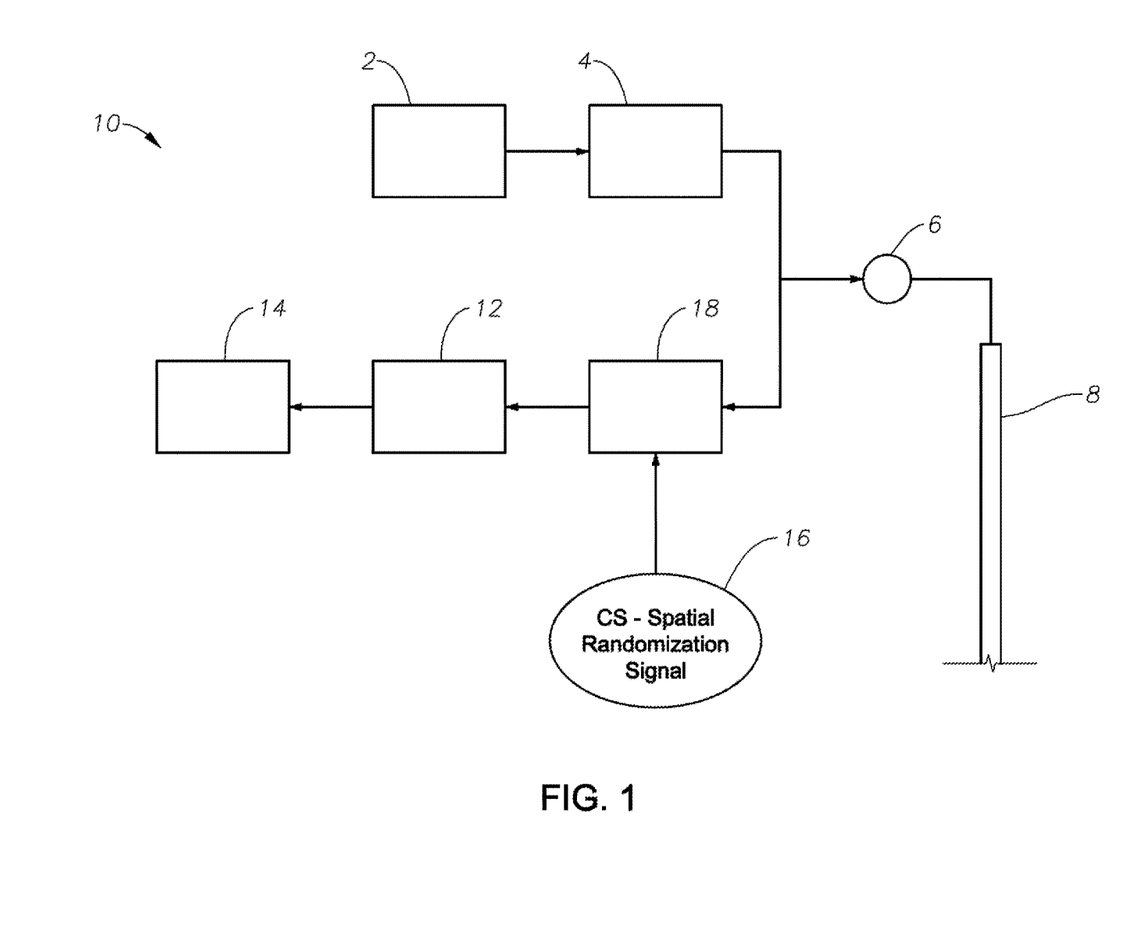
FIG. 1 is a block diagram of a distributed optical sensing system using an optical switch or shutter as a compressive sampling filter, according to certain illustrative embodiments of the present disclosure.

FIG. 1 is a block diagram of a distributed optical sensing system using an optical switch or shutter as a compressive sampling filter, according to certain illustrative embodiments of the present disclosure. In this example, distributed optical sensing system 10 includes a light source 2 to generate a light used to interrogate a waveguide 8. Light source 2 may be, for example, a laser or other suitable source of electromagnetic radiation. A modulator 4 is optically coupled in-line with light source 2 in order to pulsate or otherwise modulate the generated light. Modulator 4 is optically coupled to waveguide 8 via an optical circulator 6 which facilitates bi-directional communication of light signals. Waveguide 8 may be, for example, a fiber optic cable. During operation, light source 2 generates light that is modulated as desired by modulator 4 and sent down waveguide 8, thereby creating backscattered light signals which are sent back up waveguide 8 toward optical circulator 6 and the receiver components of system 10.

Distributed optical sensing system 10 also includes a compressive sampling filter 18 (e.g., a high-speed optical shutter or switch) to perform the function of blocking the backscattered signal from selective spatial locations of waveguide 8 (e.g., fiber optic cable) while allowing other locations to pass to the low-bandwidth receiver 12. In this embodiment, compressive sampling filter 18 is optically coupled between waveguide 8 and receiver 12. Receiver 12, because it is low bandwidth (e.g., 1 MHz, 100 KHz, etc.), will provide a measurement in proportion with the average of the combined spatial locations that are allowed by pass through compressive sampling filter 18.

To achieve this, a compressive sampling spatial randomization signal 16 is supplied to compressive sampling filter 18. A spatial randomization signal is a sequence of binary numbers generated using a pseudo-random number generator, as will be understood by those ordinarily skilled in the art having the benefit of this disclosure. Spatial randomization signal 16 enables compressive sampling filter 18 to perform pseudo-random compressive sampling by driving, in this example, an ultrafast optical shutter to open or close based on the timing of the backscattered light from the particular regions of waveguide 8 that are desired to be combined at receiver 12. An ultrafast optical shutter or switch may be one that, for example, switches or opens/closes at times below 1 ns. After the backscattered light is received at receiver 12, it is then transmitted to ADC 14 to digitize the backscattered light for processing by processing circuitry on-board or remote from ADC 14 to thereby determine one or more parameters sensed by waveguide 8.

Going back to spatial randomization signal 16, as an example, if a one meter spatial resolution is desired, the shutter of compressive sampling filter 18 may be modulated at a speed of at least 100 MHz, for example, thus blocking the backscatter light from pseudo-randomly selected one meter sections of waveguide 8. The low bandwidth (i.e., 1 MHz, 100 kHz, etc.) optical receiver 12 will provide an integration of the optical energy from many locations at once. In certain illustrative embodiments, optical receiver 12 has a bandwidth of 10 MHz or less. Thus, instead of processing each individual backscattered light energy (which requires higher bandwidth and processing capability), a plurality of backscattered light energies are combined and integrated (thus, providing allowances for lower bandwidth and processing capability). Ultimately, this measurement of the parameter being sensed by the corresponding portion of waveguide 8 may be of a significantly higher fidelity (SNR, gain, etc.) due to the use of a much lower bandwidth receiver 12 (as compared to conventional optical time domain reflector ("OTDR") methods).

In addition, these lower bandwidth components, both optical receiver 12 and low speed ADC 14, are typically much lower in cost and power consumption. ADC 14 can be lower bandwidth because receiver 12 is low bandwidth. A low bandwidth ADC may be, for example, a Texas Instruments® model ADS1675. This has benefits for embedded applications that must run off of battery power or cost sensitive applications. If it is desirable to have a spatial resolution of ½ meter, the same low-bandwidth optical receiver and ADCs can be used with the only change being that the optical shutter is modulated at twice the rate. Therefore, the bandwidth requirements of optical receiver 12 and ADC 14 discussed previously are transferred to compressive sampling filter 18.

In this illustrative embodiment, many devices may service as compressive sampling filter 18. For example, a semiconductor optical amplifier ("SOA") can act as a fast optical switch with switching times below 1 ns (1 GHz), for example, Thorlabs™ model SOA1013SXS. Other examples include electro-optic devices, such as a Lithium Niobate (LiNbO3) or Indium Phosphide (InP) waveguide in a Mach-Zehnder configuration, which can be used as an optical shutter with a bandwidth above 10 GHz. Also, acousto-optic devices, like a Bragg cell, can be used as a shutter by using the deflection properties of the Bragg cell to redirect the light passing through so that it doesn't line up with the exit fiber, thus acting as a very fast shutter. Electro-absorption modulators, for example made from InP may also be used as a high-speed shutter. Faster optical shutters using vanadium oxide (V02) may also be used which have the potential to switch at Terahertz speeds, as described in D. Johnson, *"Nanoscale Metamaterial Optical Switches Operate at Terahertz Speeds,"* IEEE Spectrum, Mar. 14, 2014. By switching at very high speeds (e.g., GHz) a spatial resolution may be provided at 10 cm or below levels while using low cost and low bandwidth optical receivers and electrical components. Moreover, in certain illustrative embodiments, in order to achieve these low spatial resolutions, it would also be necessary for the pulse width to be no greater than the desired spatial resolution.

Moreover, although not shown, the interrogation and receiving components of optical sensing system 10 are communicably coupled to processing circuitry (and may be jointly referred to as a "light detection unit"). The light detection unit may, among other functions, control the operation of the light source, spatial randomization signal, etc., as well as the processing of the received backscattered light signals for determination of sensed parameters. Therefore, the light detection units described herein may include at least one processor, a non-transitory, computer-readable storage, transceiver/network communication module, optional I/O devices, and an optional display (e.g., user interface), all interconnected via a system bus. The network communication module may be any type of communication interface such as a fiber optic interface and may communicate using a number of different communication protocols. Software instructions executable by the processor for implementing the compressive sampling described herein may be stored in suitable storage or some other computer-readable medium.

Moreover, those skilled in the art will appreciate that the disclosure may be practiced with a variety of computer-system configurations, including hand-held devices, multiprocessor systems, microprocessor-based or programmable-consumer electronics, minicomputers, mainframe computers, and the like. Any number of computer-systems and computer networks are acceptable for use with the present disclosure. The disclosure may be practiced in distributed-computing environments where tasks are performed by remote-processing devices that are linked through a communications network. In a distributed-computing environment, program modules may be located in both local and remote computer-storage media including memory storage devices. The present disclosure may therefore, be implemented in connection with various hardware, software or a combination thereof in a computer system or other processing system.

Figure 2:
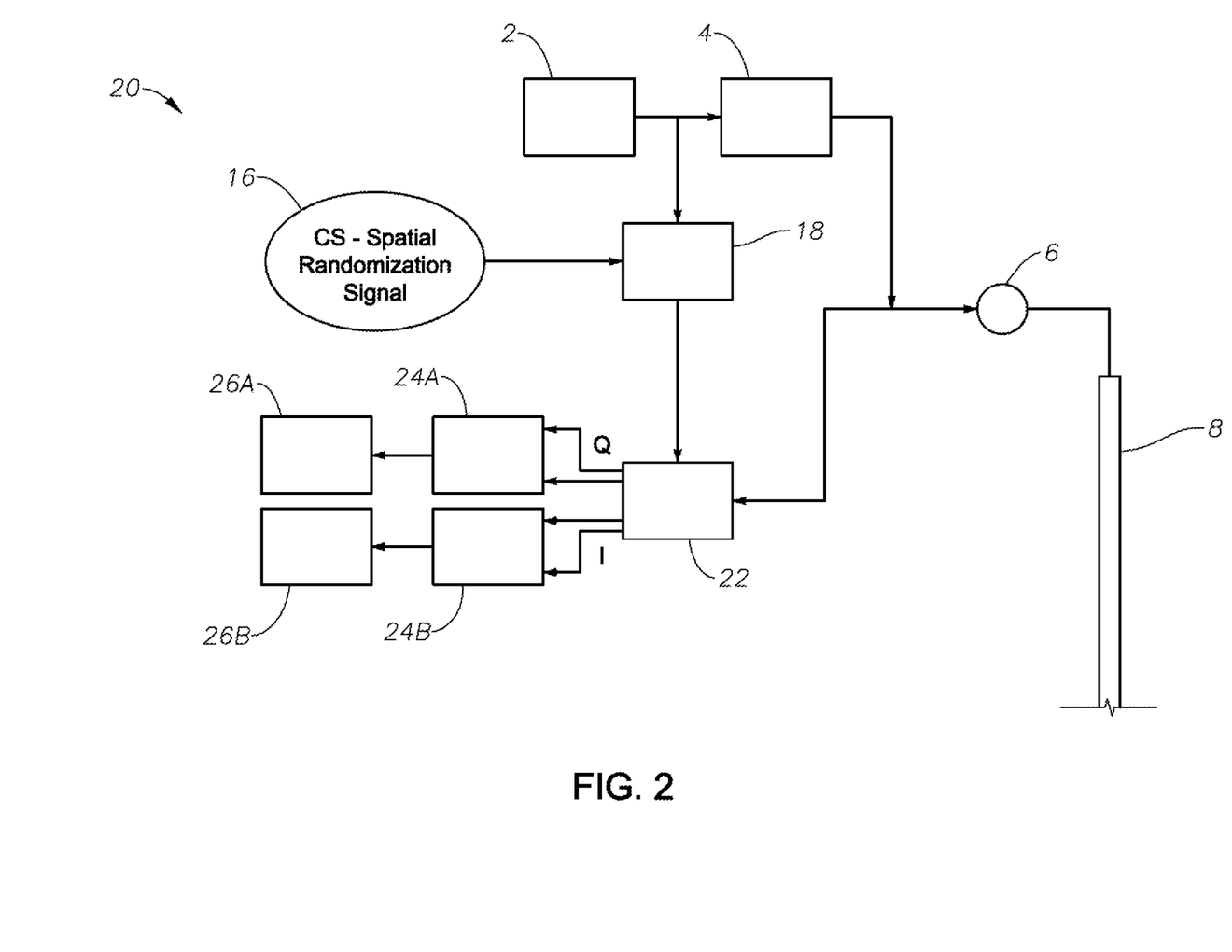
FIG. 2 is a block diagram of a distributed optical sensing system where the backscattered light is mixed with a local oscillator light, according to certain illustrative embodiments of the present disclosure.

FIG. 2 is a block diagram of a distributed optical sensing system where the backscattered light is mixed with a local oscillator light, according to certain illustrative embodiments of the present disclosure. In the case of distributed acoustic sensing, it is not necessary to position the compressive sampling filter as described in relation to FIG. 1. FIG. 2 illustrates an alternate embodiment for a distributed optical sensing system 20 whereby the backscattered light is mixed with a much more power laser light (i.e., local oscillator light). FIG. 2 is similar to the embodiment of FIG. 1, whereby like elements are identified using like numerals. However, instead of positioning compressive sampling filter 18 in-line with the backscattered light, filter 18 is positioned in-line with light source 2 (i.e., the local oscillator). Because the local oscillator light being sent to mixer 22 is much more powerful than the backscatter light being received from waveguide 8, the local oscillator (i.e., light source 2) acts as an amplifier.

By positioning compressive sampling filter 18 in-line with the local oscillator light and in front of mixer 22, instead of in-line with the backscatter light, a similar effect is created to that of FIG. 1, whereby the backscattered light was blocked. Instead, in distributed optical sensing system 20, the local oscillator light sent from source 2 is blocked by compressive sampling filter 18 at times when the spatial regions of waveguide 8 to be blocked are arriving at receiver 24 (comprised of 24A and 24B). The unblocked local oscillator light is also referred herein as "reference light." Although the local oscillator light is being selectively blocked by compressive sampling filter 18, the ultimate effect is that compressive sampling filter 18 is still utilized to selectively block portions of the backscattered light, as will be described further below.

During operation of optical sensing system 20, an optical pulse is sent into the sensing waveguide 8 using light source 2 and modulator 4, as previously discussed. As the backscatter light returns to the receiver side of system 20, it is mixed with the original laser light, called the local oscillator in a homodyne demodulator (a heterodyne scheme is also possible in alternate embodiments). The local oscillator light being passed by compressive sampling filter 18 is referred to as reference light, and is much more powerful than the backscatter light, providing a gain to the signal. The reference light is mixed in two ways in the 90 degree optical hybrid mixers 22 positioned in-line with waveguide 8. In the "I" portion of the optical hybrid light signal (also referred to as "mixed light") sent to balanced receiver 24B, the local oscillator/reference and backscatter light is mixed normally. In the Q branch of the optical hybrid light signal (also referred to as "mixed light") sent to balanced receiver 24A, the local oscillator/reference light is phase shifted by 90 degrees relative to the backscatter light signal.

By providing an I and Q interferometric signal, the optical phase can be demodulated by arctan(Q/I). In a distributed vibration or acoustic sensing system, as the waveguide is strained due to vibration, the phase of the optical backscatter signal changes. Detecting this phase change allows detecting vibration that is impacting the waveguide. The time domain multiplexing methods works here in system 20, as it does in the more general system. However, in the case of system 20, compressive sampling filter 18 (e.g., high-speed optical shutter or switch) is placed in-line with the local oscillator source 2. This has the advantage that any optical attenuation induced by compressive sampling filter 18 is not applied to the weak backscatter signal, but instead is applied to the much stronger local oscillator 2. Typically, the local oscillator power can be easily adjusted to as high of a level as needed, whereas the backscatter light is very weak and cannot be strengthened further. In fiber optic sensing system 20, when compressive sampling filter 18 is closed, the local oscillator/reference light does not mix with the backscatter light. Due to the mechanism of the 90 degree optical hybrid and balanced detector, any light signal that is not part of the mixing between local oscillator 2 and the backscatter signal is automatically subtracted out by the low bandwidth balanced detectors 24A,B, and sent to corresponding low-speed ADCs 26A,B. Therefore, when local oscillator 2 is blocked, effectively there is no interferometric light signal being detected by optical receivers 24A,B. Since this has an almost identical effect as if compressive sampling filter 18 was placed in-line with the backscatter light, compressive sampling filter 18 of system 20 still in essence selectively blocks desired portions of the backscattered light.

Accordingly, the previous illustrative embodiments utilize a compressive sampling filter optically coupled in-line with the backscatter signal or local oscillator to selectively remove the backscatter signal of selected sections of the waveguide based on the pseudo-random spatial randomization signal specified by compressive sampling. An alternative approach, however, is to apply the compressive sensing methodology to the interrogation signal instead of the backscatter signal. In the previously described illustrative systems, the pulse is equal to or less than the desired spatial resolution. For example, to achieve a one meter spatial resolution, the pulse width must be 10 ns (1 meter two-way) or less in duration. In distributed fiber optic sensing systems, there is an upper limit to the instantaneous optical power that can be sent into the fiber before negative effects occur. Primarily, the negative effects occur when exceeding the maximum power density supported by the fiber. There are several possible non-linear optical processes that are undesirable in measurement systems, which include: stimulated Raman scattering, stimulated Brillouin scattering, self-phase modulation and modulation instability. These non-linear effects set a ceiling on the optical power level of the pulse that may be used.

However, they do not set a ceiling on the total optical energy of the pulse, which is a product of the power and time duration of the pulse. To send a pulse with higher optical energy, but the same optical power, it is necessary to use a longer duration optical pulse. As the total optical energy is increased, the optical power of the backscatter signal, which contains the information being measured, will increase in proportion. The increased backscatter power will enhance the signal-to-noise ratio of the measured parameter (e.g., temperature, vibration, etc.). This has many advantages. In order to achieve a particular spatial resolution using other interrogation methods, the pulse width must be less than the spatial resolution desired. However, applying the compressive sampling methods of the present disclosure to the pulse will remove this limitation.

Figure 3:
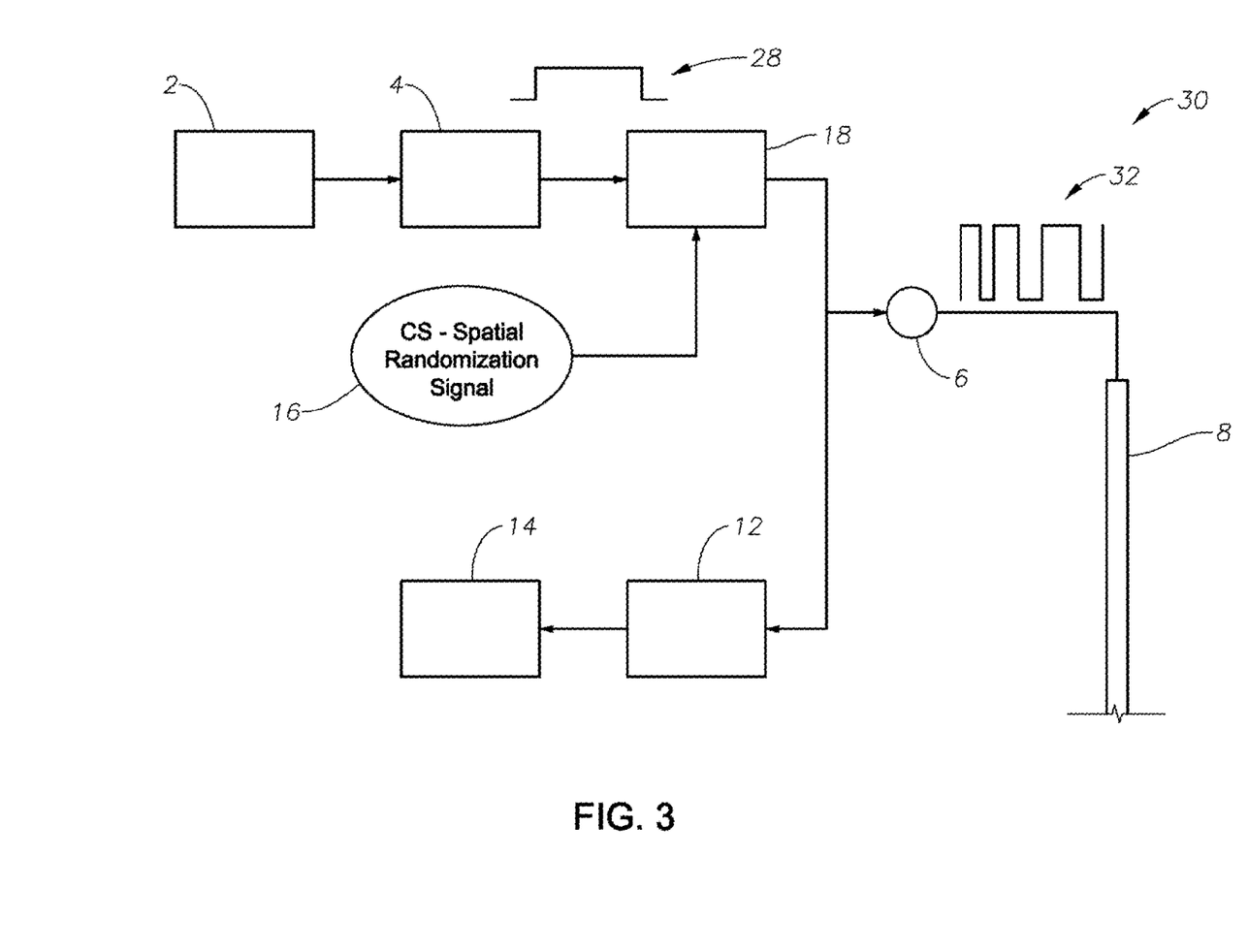
FIG. 3 illustrates a distributed optical sensing system in which compressive sampling is applied to the light pulse, according to certain illustrative alternative embodiments of the present disclosure.

Therefore, in certain alternative embodiments of the present disclosure, regions of the pulsed interrogation signal are blocked using a spatially pseudo-random filter applied in the time domain. FIG. 3 illustrates a distributed optical sensing system in which compressive sampling is applied to the light pulse, according to certain illustrative alternative embodiments of the present disclosure. The embodiment of FIG. 3 is similar to previous embodiments, where like numerals refer to like components. However, in this embodiment, distributed optical sensing system 30 includes a compressive sampling filter 18 is optically coupled between light source 2 and waveguide 8 so that the interrogation signal (i.e., the pulsed light sent from modulator 4) is selectively blocked. Here, compressive sampling filter 18 selectively blocks portion of the light pulse 28 to thereby generate a compressive sampling pulse 32.

With reference to FIG. 3, for example, at a particular time after pulse 28 is emitted from modulator 4, the backscatter light reaching receiver 12 will consist of the region of waveguide 8 that is at a distance with the two-way travel time from the interrogator equal to the time interval after pulse 28 was emitted. It is clear that at a particular moment of time after pulse 28 is emitted, the backscatter from the front of pulse 28 will be originating from a location on sensing waveguide 8 more distant than the backscatter generated by the back of pulse 28. It works out, due to the two-way travel time of the backscatter light, that the backscatter light at the receiver 12 will be exactly a combination of spatial locations that match the pattern within pulse 32 generated by compressive sampling filter 18, but with pulse 32 spatially compressed by a factor of two due to the two-way travel nature of time-domain reflectometry. Since this has an almost identical effect as if compressive sampling filter 18 was placed in-line with the backscatter light, compressive sampling filter 18 of system 30 still in essence selectively blocks desired portions of the backscattered light.

Figure 4:
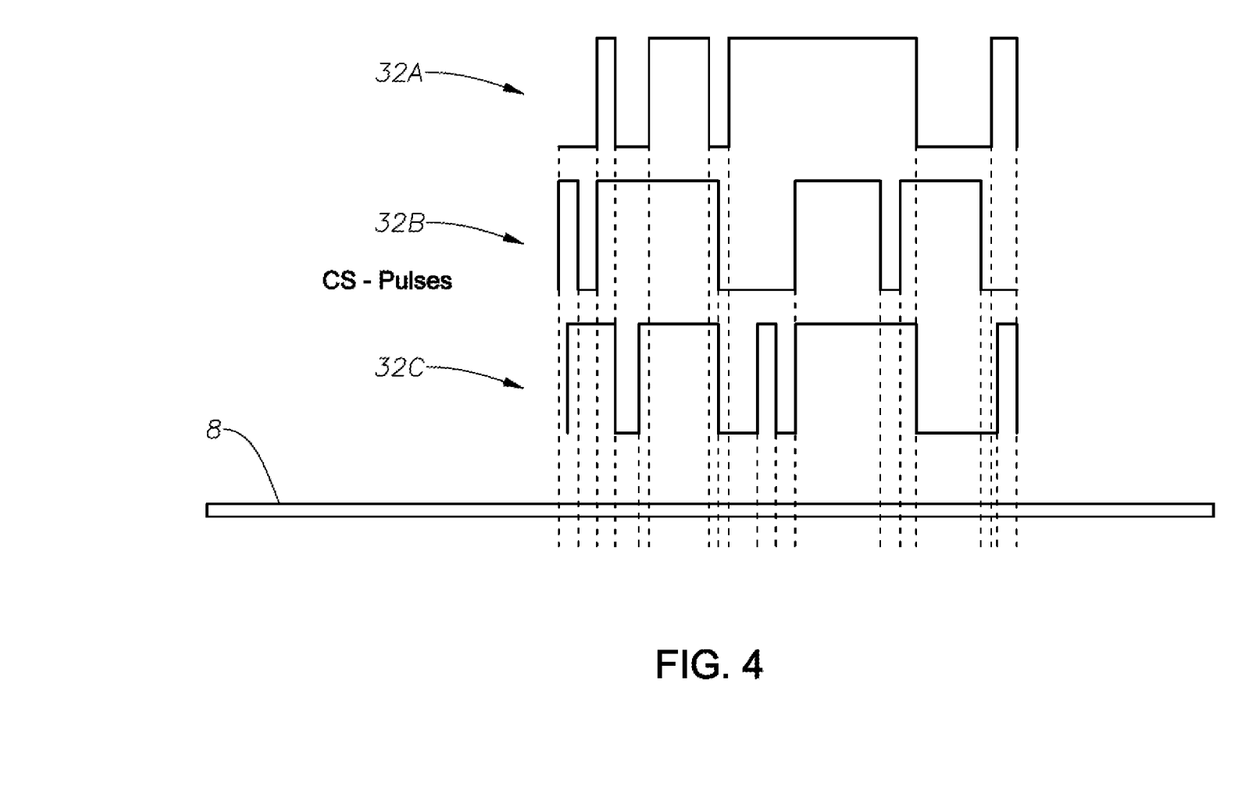
FIG. 4 is a diagram showing three different compressive sampling pulses being sent through a sensing waveguide.

Therefore, those regions of compressive sampling pulse 32 that have been blocked will represent spatial locations on waveguide 8 that are not emitting backscatter at receiver 12 at a particular moment in time, and those parts of pulse 32 that are not blocked will produce backscatter that reaches optical receiver 12 at the same moment that the blocked regions are not providing backscatter to optical receiver 12. Thus, during operation of distributed optical sensing system 30, a series of compressive sampling pulses 30A-C are sent down the fiber with a different spatial time-domain filter applied to each pulse as shown in FIGS. 3 and 4. FIG. 4 is a diagram showing three different compressive sampling pulses 32 at a particular moment overlaid on sensing waveguide 8. The diagram includes dashed lines corresponding to the regions of waveguide 8 which are providing backscatter to optical receiver 12 (high levels of pulses 32A-C) and which regions (low levels of 32A-C) are not. This is only for one instant in time. At a moment later, for example 100 ns later, the backscatter light being received at optical receiver 12 will be represented by the pulse shifted ten meters further down waveguide 8.

Therefore, the compressive sampling methods described herein can be implemented using an interrogation pulse with sections of the pulse blocked. The spatial resolution achieved with this method is based on the switching rate of the compressive sampling filter (e.g., optical switch), not on the width of the pulse. The result is that a very wide pulse (i.e., 1 microsecond or 10 microseconds, or longer), and thus a very high total energy pulse, may be emitted into the sensing waveguide. This pulse will provide a backscatter signal of much higher power than a short pulse (e.g., 10 ns or 20 ns) which is traditionally required to maintain a high spatial resolution of typically around one or two meters. By sending a series of very wide, high energy pulses, each with a pseudo-random time-domain filter applied to the pulse, the return backscatter signal collected over many pulses can be "de-compressed" via compressive sampling algorithms to achieve the original high spatial resolution, but with the benefit of a much higher signal to noise ratio provided by the higher backscatter power levels.

In conventional OTDR systems, after the pulse is launched, the system cannot launch another pulse until the original pulse has traversed to the end of the waveguide and all backscatter returns generated by that pulse have reached the optical receiver. If a second pulse was introduced before all backscatter had returned to the interrogator, the optical receiver would effectively be receiving backscatter from two locations on the fiber at the same time, thus creating a cross-talk noise problem between the two sensing locations. These two locations being received at the optical receiver would slide down the fiber over time as the two pulses traversed down the fiber.

However, with the illustrative compressive sensing methods described herein, the cross-talk problem is overcome because the locations on the waveguide that are being simultaneously received can be spatially selected by a pseudo-random spatial pattern provided by the compressive sensing spatial randomization signal. This will allow the ability to sending multiple pulses into the waveguide at once, with each pulse having a different pseudo-random spatial pattern. Extending this concept further, in certain illustrative embodiments there will be no separation in time between the end of one pseudo-random pulse and start of the next. The end effect is that pseudo-random modulated light is continuously sent into the waveguide. In this scheme, the optical backscatter power will be maximized and at any instant in time the combination of spatial locations on the waveguide being received at the optical receiver will be based on a pre-determined pseudo-random spatial pattern.

In the illustrative embodiments described herein, processing circuitry is communicably coupled to the sensing systems as previously described. The signals recorded by the optical receiver are decompressed using compressive sampling algorithms to recover the parameter being sensed (e.g., temperature, vibration, etc.) at each sensing location in the dense sensor array provided by the fiber or other waveguide, but with much higher signal to noise ratio than would be possible using conventional OTDR based sensing schemes. Illustrative compressive sampling recovery algorithms to decompress the acquired low bandwidth signal include, for example, $l_1$-norm minimization routines such as Orthogonal Matching Pursuit ("OMP") and derivatives thereof such as Stagewise OMP and Regularized OMP.

In alternative embodiments of the present disclosure, the optical sensing systems described herein may include any number of interrogation arms. For example, the backscattered light leaving optical circulator 6 may be split into several interrogation paths and process independently by a compressive sampling filter controlled by a unique spatial randomization signal. Thus, the blocked portions of the backscattered light would vary between each interrogation arm. These and other modifications of the present disclosure will be apparent to those ordinarily skilled in the art having the benefit of this disclosure.

Figure 5:
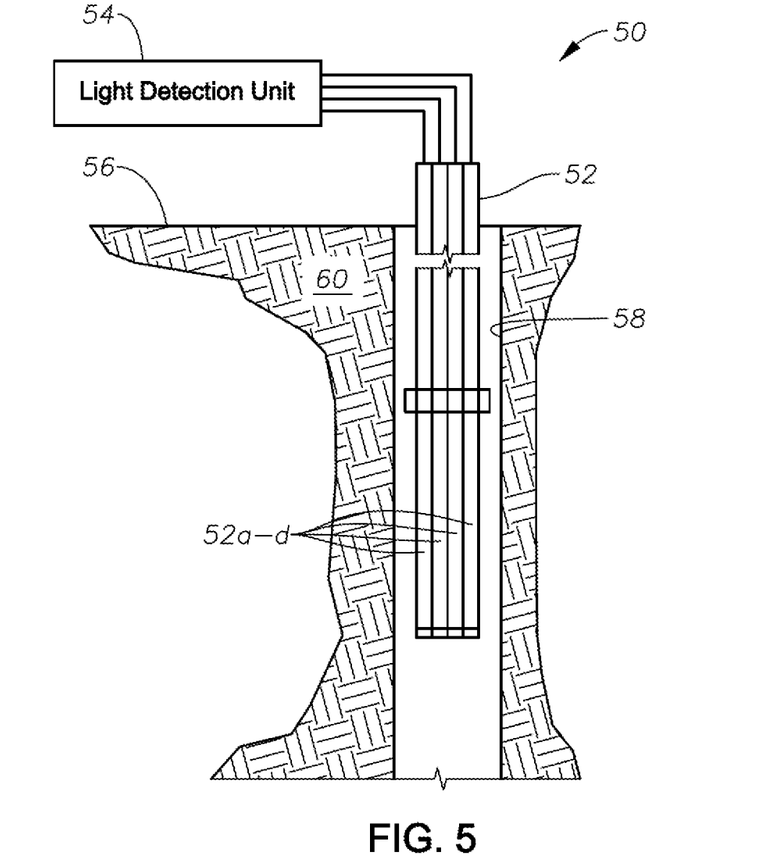
FIG. 5 is a schematic illustration of a distributed optical sensing system extending along a wellbore, according to alternative illustrative embodiments of the present disclosure.

Although the illustrative distributed optical sensing systems described herein may be used in a variety of applications, the following example will discuss a wellbore application. FIG. 5 is a schematic illustration of a distributed optical sensing system extending along a wellbore, according to alternative illustrative embodiments of the present disclosure. The waveguide may be comprised of a single waveguide or an array of waveguides. In the illustrated embodiment, however, distributed optical sensing system 50 includes waveguide detector 52 that is comprised of an array of waveguides 52a-d. Distributed optical sensing system 50 includes a light detection unit 54 positioned at a surface location 56. In other embodiments, however, light detection unit 54 may be positioned downhole. Light detection unit 54 is part of the signal processing chain, and may be any of the interrogation and receiving components of the compressive sensing system described herein.

Light detection unit 54 described herein may include at least one processor, a non-transitory, computer-readable storage, transceiver/network communication module, optional I/O devices, and an optional display (e.g., user interface), all interconnected via a system bus. The network communication module may be any type of communication interface such as a fiber optic interface and may communicate using a number of different communication protocols. Software instructions executable by the processor for implementing the compressive sensing described herein may be stored in suitable storage or some other computer-readable medium.

Moreover, those skilled in the art will appreciate that the disclosure may be practiced with a variety of computer-system configurations, including hand-held devices, multi-processor systems, microprocessor-based or programmable-consumer electronics, minicomputers, mainframe computers, and the like. Any number of computer-systems and computer networks are acceptable for use with the present disclosure. The disclosure may be practiced in distributed-computing environments where tasks are performed by remote-processing devices that are linked through a communications network. In a distributed-computing environment, program modules may be located in both local and remote computer-storage media including memory storage devices. The present disclosure may therefore, be implemented in connection with various hardware, software or a combination thereof in a computer system or other processing system.

Nevertheless, light detection unit 54 is optically coupled to waveguide detector 52, which may be transparent optical fibers that extend over a desired range without significant reduction in light intensity. Waveguide detector 52 extends down a wellbore 58 which has been drilled in a formation 60. During operation of the embodiment of FIG. 5, the interrogation signals are sent from light detection unit 54, received and processed using the compressive sampling methods described herein to determine one or more parameters of the downhole environment (e.g., pressure, temperature, etc.).

The wellbore application illustrated in FIG. 5 may take a variety of forms. For example, the application may be an onshore oil or gas drilling rig in which the distributed optical sensing system has been permanently or temporarily positioned along the wellbore. In certain embodiments, the waveguide may form part of a casing string. In other embodiments, the waveguide may be embedded within the cement used to secure the casing in place. In other applications, the waveguide(s) may be deployed along a wireline or other conveyance (e.g., logging-while-drilling or measurement-while-drilling assembly, or some other suitable downhole string). In yet other embodiments, the waveguide(s) may be positioned inside the casing or may form part of an inner string, such as, for example, part of a production string. There are a variety of other ways in which these components may be permanently or temporarily positioned downhole, as these are only illustrative in nature.

Accordingly, the foregoing embodiments provide many advantages. The disclosed compressive sampling optical systems can be used to provide unprecedented spatial resolution (sub-centimeter DTS, for example), or configured to provide very high signal-to-noise ratio backscatter signaling while maintaining typical spatial resolution of one or two meters. The illustrative embodiments may be applied to any distributed fiber optic sensing method that utilizes optical time-domain multiplexing methods.

Embodiments described herein further relate to any one or more of the following paragraphs:

1. A distributed optical sensing system, comprising a light source to generate light; a waveguide positioned to optically interact with the light to produce backscattered light; a compressive sampling filter positioned to selectively block portions of the light or the backscattered light based upon a compressive sampling technique; and an optical receiver to receive the backscattered light.

2. A system as defined in paragraph 1, wherein the compressive sampling filter is an optical switch or optical shutter.

3. A system as defined in paragraphs 1 or 2, wherein the compressive sampling filter is optically coupled between the waveguide and the optical receiver to selectively block portions of the backscattered light.

4. A system as defined in any of paragraphs 1-3, wherein the optical receiver has a bandwidth of 10 MHz or less.

5. A system as defined in any of paragraphs 1-4, wherein the compressive sampling filter is optically coupled between a local oscillator and a mixer to selectively block portions of the backscattered light.

6. A system as defined in any of paragraphs 1-5, wherein the mixer is a 90 degree hybrid mixer.

7. A system as defined in any of paragraphs 1-6, wherein the optical receiver is a balanced optical receiver.

8. A system as defined in any of paragraphs 1-7, wherein the compressive sampling filter is optically coupled between the light source and the waveguide to selectively block portions of the light.

9. A system as defined in any of paragraphs 1-8, wherein the light source generates a light pulse having width of 1 microsecond or longer.

10. A system as defined in any of paragraphs 1-9, further comprising processing circuitry communicably coupled to the receiver to receive the backscattered light and thereby determine a parameter being sensed by the waveguide.

11. A system as defined in any of paragraphs 1-10, wherein the waveguide is positioned along a wellbore.

12. A system as defined in any of paragraphs 1-11, wherein the waveguide is a fiber optic cable.

13. A distributed optical sensing method, comprising generating light that optically interacts with a waveguide to produce backscattered light; selectively blocking portions of the light or the backscattered light using a compressive sampling filter; and analyzing the backscattered light to thereby determine a parameter being sensed by the waveguide.

14. A method as defined in paragraph 13, wherein selectively blocking the backscattered light comprises optically interacting the backscattered light with the compressive sampling filter.

15. A method as defined in paragraphs 13 or 14, wherein selectively blocking the backscattered light comprises using an optical switch or optical shutter to selectively block the backscattered light.

16. A method as defined in any of paragraphs 13-15, wherein selectively blocking the backscattered light comprises optically interacting a local oscillator light with the compressive sampling filter to produce a reference light;

optically interacting the reference and backscattered light with a mixer to produce mixed light; and optically interacting the mixed light with the receiver to thereby generate the backscattered light.

17. A method as defined in any of paragraphs 13-16, wherein optically interacting the backscattered light further comprises phase shifting the reference light 90 degrees relative to the backscattered light.

18. A method as defined in any of paragraphs 13-17, wherein selectively blocking the backscattered light comprises optically interacting the light with the compressive sampling filter to produce a compressive sampling pulse having blocked regions.

19. A method as defined in any of paragraphs 13-18, wherein generating the light comprises generating a light having a pulse width of 1 microsecond or longer.

20. A method as defined in any of paragraphs 13-19, wherein determining the parameter comprises determining a parameter along a wellbore.

21. A distributed optical sensing method, comprising interrogating a sensing waveguide using an interrogation signal; receiving backscattered signals from selected regions of the sensing waveguide based upon a compressive sampling technique; and using the backscattered signals, determining a parameter being sensed by the sensing waveguide.

22. A method as defined in paragraph 21, wherein receiving backscattered signals comprises selectively blocking portions of the backscattered signals using a compressive sampling filter positioned in-line with the sensing waveguide.

23. A method as defined in paragraphs 21 or 22, wherein receiving backscattered signals comprises selectively blocking portions of a local oscillator light.

24. A method as defined in any of paragraphs 21-23, wherein receiving backscattered signals comprises mixing the backscattered light with a reference signal.

25. A method as defined in any of paragraphs 21-24, wherein receiving backscattered signals comprises selectively blocking portions of the interrogation signal.

26. A method as defined in any of paragraphs 21-25, wherein a wellbore parameter is determined.

Although various embodiments and methodologies have been shown and described, the disclosure is not limited to such embodiments and methodologies and will be understood to include all modifications and variations as would be apparent to one skilled in the art. Therefore, it should be understood that the disclosure is not intended to be limited to the particular forms disclosed. Rather, the intention is to cover all modifications, equivalents and alternatives falling within the spirit and scope of the disclosure as defined by the appended claims.

What is claimed is:

1. A distributed optical sensing system, comprising:
a light source to generate light;
a waveguide positioned to optically interact with the light to produce backscattered light;
a compressive sampling filter positioned to selectively block portions of the light or the backscattered light based upon a compressive sampling technique; and
an optical receiver to receive the backscattered light.

2. A system as defined in claim 1, wherein the compressive sampling filter is an optical switch or optical shutter.

3. A system as defined in claim 1, wherein the compressive sampling filter is optically coupled between the waveguide and the optical receiver to selectively block portions of the backscattered light.

4. A system as defined in claim 1, wherein the optical receiver has a bandwidth of 10 MHz or less.

5. A system as defined in claim 1, wherein the compressive sampling filter is optically coupled between a local oscillator and a mixer to selectively block portions of the backscattered light.

6. A system as defined in claim 5, wherein the mixer is a 90 degree hybrid mixer.

7. A system as defined in claim 5, wherein the optical receiver is a balanced optical receiver.

8. A system as defined in claim 1, wherein the compressive sampling filter is optically coupled between the light source and the waveguide to selectively block portions of the light.

9. A system as defined in claim 8, wherein the light source generates a light pulse having width of 1 microsecond or longer.

10. A system as defined in claim 1, further comprising processing circuitry communicably coupled to the receiver to receive the backscattered light and thereby determine a parameter being sensed by the waveguide.

11. A system as defined in claim 1, wherein the waveguide is positioned along a wellbore.

12. A system as defined in claim 1, wherein the waveguide is a fiber optic cable.

13. A distributed optical sensing method, comprising:
generating light that optically interacts with a waveguide to produce backscattered light;
selectively blocking portions of the light or the backscattered light using a compressive sampling filter; and
analyzing the backscattered light to thereby determine a parameter being sensed by the waveguide.

14. A method as defined in claim 13, wherein selectively blocking the backscattered light comprises optically interacting the backscattered light with the compressive sampling filter.

15. A method as defined in claim 13, wherein selectively blocking the backscattered light comprises using an optical switch or optical shutter to selectively block the backscattered light.

16. A method as defined in claim 13, wherein selectively blocking the backscattered light comprises:
optically interacting a local oscillator light with the compressive sampling filter to produce a reference light;
optically interacting the reference and backscattered light with a mixer to produce mixed light; and
optically interacting the mixed light with the receiver to thereby generate the backscattered light.

17. A method as defined in claim 16, wherein optically interacting the backscattered light further comprises phase shifting the reference light 90 degrees relative to the backscattered light.

18. A method as defined in claim 13, wherein selectively blocking the backscattered light comprises optically interacting the light with the compressive sampling filter to produce a compressive sampling pulse having blocked regions.

19. A method as defined in claim 18, wherein generating the light comprises generating a light having a pulse width of 1 microsecond or longer.

20. A method as defined in claim 13, wherein determining the parameter comprises determining a parameter along a wellbore.

21. A distributed optical sensing method, comprising:
interrogating a sensing waveguide using an interrogation signal;

receiving backscattered signals from selected regions of the sensing waveguide based upon a compressive sampling technique; and using the backscattered signals, determining a parameter being sensed by the sensing waveguide.

22. A method as defined in claim 21, wherein receiving backscattered signals comprises selectively blocking portions of the backscattered signals using a compressive sampling filter positioned in-line with the sensing waveguide.

23. A method as defined in claim 21, wherein receiving backscattered signals comprises selectively blocking portions of a local oscillator light.

24. A method as defined in claim 21, wherein receiving backscattered signals comprises mixing the backscattered light with a reference signal.

25. A method as defined in claim 21, wherein receiving backscattered signals comprises selectively blocking portions of the interrogation signal.

26. A method as defined in claim 21, wherein a wellbore parameter is determined.

\* \* \* \* \*